United States Patent [19]

Colvin

[11] Patent Number: 4,532,011
[45] Date of Patent: Jul. 30, 1985

[54] INHIBITING POLYMERIZATION OF VINYLAROMATIC MONOMERS

[75] Inventor: Howard A. Colvin, Akron, Ohio

[73] Assignee: The Goodyear Tire & Rubber Company, Akron, Ohio

[21] Appl. No.: 585,801

[22] Filed: Mar. 2, 1984

[51] Int. Cl.³ .......................... B01D 3/34; C07C 7/20
[52] U.S. Cl. .......................................... 203/9; 203/60; 203/8; 585/5; 585/807
[58] Field of Search .................. 203/9, 7, 8, 6, 60; 585/1, 2, 3, 4, 5, 10, 800, 860, 258, 807, 810; 436/7; 524/458

[56] References Cited

U.S. PATENT DOCUMENTS

| | | | |
|---|---|---|---|
| 2,556,030 | 6/1951 | Coulter et al. | 203/9 |
| 3,733,326 | 5/1973 | Murayama et al. | 585/2 |
| 3,763,018 | 10/1973 | Raff et al. | 203/9 |
| 3,964,978 | 6/1976 | Watson | 203/9 |
| 4,021,310 | 5/1977 | Shimizu et al. | 203/8 |
| 4,056,006 | 11/1977 | Smith et al. | 436/7 |
| 4,376,678 | 3/1983 | Partos | 203/9 |
| 4,390,741 | 6/1983 | Colvin et al. | 585/258 |
| 4,439,278 | 3/1984 | Douglas et al. | 203/9 |
| 4,465,881 | 8/1984 | Miller et al. | 585/4 |
| 4,474,923 | 10/1984 | Keskey et al. | 524/458 |
| 4,481,122 | 11/1984 | Root et al. | 585/10 |

*Primary Examiner*—S. Leon Bashore
*Assistant Examiner*—Virginia Manoharan
*Attorney, Agent, or Firm*—D. O. Nickey

[57] ABSTRACT

Vinylaromatic compounds are stabilized against undesired polymerization by adding to the vinylaromatic compounds small amounts of zinc or nickel salts of dialkyl dithiocarbamates, specifically p-diisopropylbenzene can be stabilized by the use of zinc dibutyldithiocarbamate.

7 Claims, No Drawings

INHIBITING POLYMERIZATION OF VINYLAROMATIC MONOMERS

TECHNICAL FIELD

The present invention relates to the stabilization of ethylenically unsaturated compounds, more particularly, to the inhibition of undesired polymerization of vinylaromatic compounds during storage, shipping or processing. Specifically, this invention relates to the use of zinc or nickel salts of dialkyl-dithiocarbamates as a polymerization inhibitor for the processing of dialkenylbenzene.

BACKGROUND ART

Vinylaromatic compounds such as styrene and diisopropenylbenzene undergo undesired spontaneous polymerization (ie. polymerization of monomers due to random generation of free radicals in the monomers) during storage, shipping or processing. The problem of undesired polymerization of monomer is particularly acute during purification operations. Spontaneous polymerization is disadvantageous because it causes foulling of distillation column reboilers and other equipment used for processing vinylaromatic monomers. In addition, spontaneous polymerization is an economic burden that results in loss of monomer and a decrease in overall process efficiency. Thus, there is a need to inhibit the spontaneous polymerization of vinylaromatic monomers, more specifically, dialkenylbenzenes.

To prevent spontaneous polymerization of vinylaromatic monomers, it is a common practice to add to monomers certain polymerization inhibiting compounds. A wide variety of such compounds, known as polymerization inhibitors, have been used for this purpose. Sulfur has been widely used in the past to inhibit polymerization of vinylaromatic compounds. However, sulfur usage is undesirable because relatively large quantities of sulfur are required for effective polymerization inhibition. This presents a waste removal problem when the monomer is separated from the sulfur monomer mixture by distillation. The distillation bottoms product which contains high molecular weight polymer and sulfur cannot be conveniently burned due to the potential air pollution hazard caused by sulfur oxides. Thus, this material must be disposed of by burial in a waste dump.

Many chemical compounds have been developed as substitutes for sulfur in polymerization inhibiting applications. These compounds have been used as polymerization inhibitors for vinylaromatic monomers with varying degrees of success. U.S. Pat. No. 3,390,198 discloses the use of several mono- and di-alkylcatechols as polymerization inhibitors for hot styrene. U.S. Pat. Nos. 4,061,545 and 4,177,110 disclose the use of a combination of tertiary butylcatechols and phenothiazine as a polymerization inhibitor system for vinylaromatic compounds.

U.S. Pat. No. 4,409,480 is concerned with the use of compounds such as N-dialkylhydroxylamines and tertiary alkylcatechols and their synergistic effect as a stabilization system for vinylaromatic compounds. U.S. Pat. No. 4,389,285 discloses an improved method for preparing and processing ethylenically unsaturated aromatic monomers, in that 3,5-dinitrosalicylic acid as used as a process inhibitor.

The styrene industry currently employs 4,6-dinitro-ortho-cresol as a process inhibitor. However, this compound is a highly toxic material. The toxicity of this chemical raises exposure concerns with regard to monomer production and the preparation of the chemical itself. Therefore, there exists a need in the industry for a process inhibitor to replace those presently accepted process inhibitors that are toxic or have other shortcomings.

Vinylaromatic monomers such as styrene, alpha-alkylstyrene, vinyltoluene, divinylbenzene, meta- and para-diisopropenylbenzene are important for their ability to form useful polymeric materials. These compounds are typically prepared by catalytic dehydrogenation of alkylaromatic compounds having corresponding carbon chains. The crude product of the dehydrogenation reaction, however, is a mixture of materials comprising in addition to the desired vinyl or divinylaromatic monomer various alkylaromatic compounds. These other substances must be separated from the monomer to obtain a commercially useful product.

It has now been discovered that dithiocarbamates, more specifically, zinc or nickel dialkyldithiocarbamates provide outstanding polymerization inhibiting activity for vinylaromatic monomers, more specifically, dialkenylbenzenes. Thus, because of the properties of zinc or nickel dialkyldithiocarbamate, it is now possible to provide superior polymerization inhibiting protection over those materials presently accepted in the industry.

The present invention provides stable compositions of vinylaromatic monomers and a method for effectively and economically inhibiting spontaneous polymerization of styrene, vinylaromatic monomers and, more specifically, meta- and para-diisopropenylbenzenes.

DISCLOSURE OF THE INVENTION

There is disclosed an improvement in the processes for the preparation of readily polymerizable ethylenically unsaturated aromatic compounds wherein the improvement comprises employing zinc or nickel dialkyldithiocarbamates as polymerization inhibitors, wherein the alkyl radicals can be from 1 to 10 carbon atoms.

The present invention relates to the use of zinc or nickel dialkyldithiocarbamates, more specifically, zinc dialkyldithiocarbamates as polymerization inhibitors in the preparation of readily polymerizable ethylenically unsaturated aromatic compounds. As used herein, the term "process inhibitor" refers to a polymerization inhibitor which is employed during the preparation and processing of the monomer.

The present invention is applicable to readily polymerizable ethylenically unsaturated aromatic compounds. Such compounds include: meta- and para-diisopropenylbenzene, styrene, α-methylstyrene, vinyltoluene, vinylnaphthalene, divinylbenzene, etc. Compounds preferred for use in the process of the present invention include diisopropenylbenzene and α-methylstyrene with diisopropenylbenzene being particularly preferred. While portions of the present specification refer specifically to diisopropenylbenzene as an illustrative member of this class of compounds, it is to be understood that this specification applies to all members of the described class of readily polymerizable ethylenically unsaturated aromatic compounds.

During the later stages of current processes for the production of ethylenically unsaturated aromatic compounds, the crude monomer is typically subjected to vacuum distillation in order to remove excess reactants and other volatile aromatic impurities. In accordance with the process of the present invention zinc or nickel dialkyldithiocarbamates are employed as a process inhibitor during the preparation of the monomer and especially during the distillation step, which is when polymerization is most likely to occur.

The zinc or nickel dialkyldithiocarbamates can be supplied to the process in a variety of ways. The dithiocarbamate is normally mixed with the crude reactor effluent before distillation. In this manner the reaction product is protected throughout the entire distillation process.

The zinc or nickel dialkyldithiocarbamates are provided to the reaction system in an amount which is sufficient to effect the inhibition of polymerization. Typically, the zinc or nickel dialkyldithiocarbamate will be present in an amount of about 10 to 3000 ppm (parts per million) based upon the weight of reactants and products present in the distillation column. Preferably, the dithiocarbamate is present in a concentration of from 250 to 2000 ppm with a concentration of from 500 to 1000 ppm being especially preferred.

The dithiocarbamates can be provided to the diisopropenylbenzene preparation process either directly or as a stock solution. Zinc dialkyldithiocarbamate is sufficiently soluble in a suitable carrier solvents to allow the preparation of such a stock solution. Suitable carrier solvents are the chlorinated hydrocarbons, such as chloroform. The use of stock solutions as process inhibitors is well known in the art and is a wide spread practice.

Additional inhibitors may also be present during the process of the present invention. For example, product inhibitors such as t-butylcatechol may also be present during the preparation and/or distillation of the crude monomer.

The zinc or nickel dialkyldithiocarbamates can be made by the reaction of secondary amines with carbon disulfide in the presence of a metal hydroxide according to the following reaction:

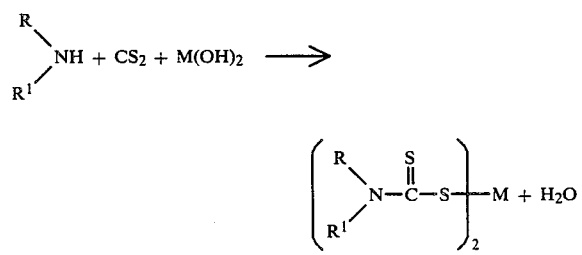

wherein $R + R^1$ can be the same or different radical of 1 to 10 carbon atoms and M is zinc or nickel. For more information see: Dimitri Coucouranis, *Progress in Inorganic Chemistry*, Vol. 11, p. 240ff.

The following examples will serve to further illustrate the invention. Unless otherwise stated parts and percentages are on a weight basis. In the examples, diisopropenylbenzene, which is representative of divinylaromatic monomers, was used as the test monomer.

EXPERIMENT I

The data in the following Table I was obtained by heating a sample of pure diisopropenylbenzene at 150° C. under nitrogen in the presence of 1000 ppm of inhibitor and sampling every hour.

TABLE I

Percentage loss of p-Diisopropenylbenzene at 150° C.

| Time | t-Butyl-catechol | 4-6-dinitro-ortho cresol | dinitro-p-cresol | Pheno-thiazine | Zinc Dibutyl-dithio-carbamate |
|---|---|---|---|---|---|
| 1 hr | 2.0 | 0.6 | 3.2 | 1.3 | 0 |
| 2 hr | 3.3 | 2.8 | 4.9 | 1.2 | 0.6 |
| 3 hr | 4.4 | 4.2 | 4.8 | 3.5 | 2.8 |
| 4 hr | 4.6 | 5.8 | 5.3 | 5.6 | 2.7 |
| 5 hr | 5.1 | 5.8 | 7.8 | 6.1 | 5.9 |
| 6 hr | 7.6 | 7.0 | 8.0 | 6.8 | 5.8 |
| 7 hr | 8.5 | 7.9 | 10.4 | 8.1 | 6.7 |
| 8 hr | 8.4 | 10.9 | 10.3 | 8.6 | 5.6 |

The data presented in Table I demonstrates that zinc dibutyldithiocarbamate provides excellent initial and prolonged protection from undesirable polymerization of p-diisopropenylbenzene. It is unexpected that zinc dibutyldithiocarbamate would provide better protection than stabilizers presently used in the industry.

EXPERIMENT II

The use of zinc dialkyldithiocarbamates and other stabilizers was investigated as an inhibitor for the monomer, m-diisopropenylbenzene, using the procedure set out in Experiment I. The results of the experiment are set out in Table II.

TABLE II

Percentage loss of m-Diisopropenylbenzene at 150° C.

| Time | No Inhibitor | t-Butyl-catechol | 4,6-dinitro-ortho cresol | dinitro-p-cresol | Pheno-thiazine | Zinc Dibutyl-dithiocarbamate |
|---|---|---|---|---|---|---|
| 1 hr | 0.0 | 0.0 | 1.2 | 2.3 | 2.6 | 0.6 |
| 5 hr | 2.3 | 3.5 | 1.6 | 5.8 | 5.4 | 2.0 |
| 8 hr | 4.9 | 2.4 | 2.7 | 8.6 | 8.5 | 3.1 |

EXPERIMENT III

The use of other metals besides zinc was investigated in conjunction with other alkyl groups. The procedure of Experiment I was followed and the data is presented in Table III.

TABLE III

% Loss of p-diisopropenylbenzene at 150° C. after 1 hour

| Compound | % lost to Polymer |
|---|---|
| (1) Cu dibutyl DTC* | 2.4 |
| (2) Ni dibutyl DTC | 0.5 |
| (3) Tin dibutyl DTC | 1.1 |
| (4) Zn diethyl DTC | 0.7 |
| (5) Na diisopropyl DTC | 1.3 |
| (6) Tetra methyl thiauram disulfide | 1.9 |
| (7) Zn dibutyl DTC | 0.0 |
| (8) None (control) | 0.6 |

*dithiocarbamate

It is evident from the data presented that zinc dibutyldithiocarbamate shows a marked improvement over all inhibitors for the stabilization of p-diisopropenylbenzene and is also effective for the meta isomer. Thus, the process of the instant invention provides an inhibitor wherein diisopropenylbenzene losses are minimized and purification is made much easier. The use of zinc dibutyldithiocarbamate has been successful in the distillation of para-diisopropenylbenzene on a pilot plant scale, thus indicating potential commercial success.

Although the invention is described with particular reference to specific examples, it is to be understood that the invention includes obvious variance, e.g., the inhibitor can be formulated to contain more than one member from the specified class of compounds.

What is claimed is:

1. A composition comprised of (a) a m or p-diisopropenylbenzene monomer and (b) at least one compound selected from the group consisting of zinc dialkyldithiocarbamates at a concentration of 10 to 3000 ppm, wherein the alkyl radical can be from one to ten carbon atoms.

2. The composition of claim 1 wherein the dithiocarbamate is zinc dibutyldithiocarbamate.

3. A process for inhibiting polymerization of a m or p-diisopropenylbenzene comprising adding to the said monomer an amount of a polymerization inhibiting agent effective to substantially reduce the rate of polymerization, the improvement comprising using as the agent zinc dibutyldithiocarbamate present at a concentratin of 10 to 3000 ppm.

4. A process for inhibiting the formation of polymerized m or p-diisopropenylbenzene monomer during distillative purification of said monomer comprising distilling said monomer in the presence of zinc dialkyldithiocarbamate at a concentration of 10 to 3000 ppm, wherein the alkyl radical can be from 1 to 10 carbon atoms.

5. A process according to claim 4 wherein said dialkyldithiocarbamate is zinc dibutyldithiocarbamate.

6. A process according to claim 3 wherein said zinc dibutyldithiocarbamate is present in a concentration of 50 to 3000 ppm.

7. A process according to claim 3 wherein said monomer is p-diisopropenylbenzene and said zinc dibutyldithiocarbamate is at a concentration of 500 to 2000 ppm.

* * * * *